`United States Patent` [19]

Yoon

[11] Patent Number: 5,573,511

[45] Date of Patent: Nov. 12, 1996

[54] RETRACTABLE SAFETY PENETRATING INSTRUMENT WITH SAFETY PROBE

[76] Inventor: InBae Yoon, 2101 Highland Ridge Dr., Phoenix, Md. 21131

[21] Appl. No.: 395,609

[22] Filed: Feb. 28, 1995

Related U.S. Application Data

[63] Continuation-in-part of Ser. No. 247,205, May 20, 1994, and Ser. No. 245,007, Aug. 10, 1994, Pat. No. 5,478,317, which is a continuation of Ser. No. 800,507, Nov. 27, 1991, abandoned, said Ser. No. 247,205, is a division of Ser. No. 800,507.

[51] Int. Cl.$^6$ .................................................. A61M 5/00
[52] U.S. Cl. ........................................... 604/164; 604/169
[58] Field of Search .................................. 604/164, 165, 604/170, 117, 169, 264; 606/184, 185, 191

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,802,275 | 4/1989 | Haber et al. . |
| 4,817,603 | 4/1989 | Turner et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |

(List continued on next page.)

FOREIGN PATENT DOCUMENTS

| | | |
|---|---|---|
| 2544262 | 4/1977 | Germany . |
| 1435246 | 11/1988 | U.S.S.R. . |

*Primary Examiner*—Todd E. Manahan

[57] ABSTRACT

A safety penetrating instrument for establishing a portal in the wall of an anatomical cavity includes a housing, a portal sleeve, a penetrating member disposed within the portal sleeve and movable relative thereto between an extended position where a distal end of the penetrating member protrudes from a distal end of the portal sleeve and a retracted position proximally spaced from the extended position, a distally-biased safety probe disposed within the penetrating member and movable relative thereto between an extended safety probe rest position protecting the penetrating member distal end when the penetrating member is retracted and a safety probe retracted position exposing the penetrating member distal end when the penetrating member is extended, a retracting mechanism for moving the penetrating member from its extended position to its retracted position, a handle or knob for manually moving the penetrating member from the its retracted position to its extended position, a locking mechanism for locking the penetrating member in its extended position, and a releasing mechanism responsive to penetration of the safety penetrating instrument into the anatomical cavity for triggering release of the locking mechanism to permit the retracting mechanism to move the penetrating member proximally to its retracted position.

42 Claims, 4 Drawing Sheets

U.S. PATENT DOCUMENTS

| | | |
|---|---|---|
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 9/1992 | Shichman . |
| 5,114,407 | 5/1992 | Burbank . |
| 5,116,353 | 5/1992 | Green . |
| 5,127,909 | 7/1992 | Shichman . |
| 5,129,885 | 7/1992 | Green et al. . |
| 5,152,754 | 10/1992 | Plyley et al. . |
| 5,158,552 | 10/1922 | Borgia et al. . |
| 5,207,647 | 5/1993 | Phelps . |
| 5,226,426 | 7/1993 | Yoon . |
| 5,226,891 | 7/1993 | Bushatz et al. . |
| 5,290,240 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl, Jr. . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,342,382 | 8/1994 | Brinkerhoff et al. . |
| 5,346,459 | 9/1994 | Allen . |
| 5,350,393 | 9/1994 | Yoon . |
| 5,360,405 | 11/1994 | Yoon . |
| 5,372,588 | 12/1994 | Farley et al. . |
| 5,376,082 | 12/1994 | Phelps . |

FIG. 9

The present invention is generally characterized in a safety penetrating instrument for establishing a portal in the wall of an anatomical cavity including a housing, a portal sleeve fixedly secured to the housing, a penetrating member disposed within the portal sleeve and movable relative to the portal sleeve between an extended position where a distal end of the penetrating member protrudes distally from a distal end of the portal sleeve and a retracted position proximally spaced from the extended position, a distally-biased safety probe disposed within the penetrating member and movable relative to the portal sleeve between an extended safety probe rest position protecting the penetrating member distal end when the penetrating member is retracted and a safety probe retracted position exposing the penetrating member distal end when the penetrating member is extended, retracting means for moving the penetrating member from the penetrating member extended position to the penetrating member retracted position, means for manually moving the penetrating member from the penetrating member retracted position to the penetrating member extended position, locking means for locking the penetrating member in the penetrating member extended position while permitting a predetermined amount of proximal movement of the penetrating member during penetration of the anatomical cavity wall, penetrating member bias means for biasing the penetrating member distally in the locked penetrating member extended position to permit the penetrating member to move proximally during penetration of the anatomical cavity wall and distally upon introduction into the anatomical cavity, and releasing means responsive to penetration of the safety penetrating instrument into the anatomical cavity for triggering release of the locking means to permit the retracting means to move the penetrating member to the penetrating member retracted position.

Another aspect of the present invention is generally characterized in a safety penetrating instrument for establishing a portal in the wall of an anatomical cavity including a housing, a distally-biased portal sleeve movable relative to the housing between an extended rest position and a proximally spaced retracted position, a penetrating member disposed within the portal sleeve and movable relative to the portal sleeve between an extended position where a distal end of the penetrating member protrudes distally from a distal end of the portal sleeve and a retracted position proximally spaced from the extended position, a distally-biased safety probe disposed within the penetrating member and movable relative to the penetrating member between an extended safety probe rest position protecting the penetrating member distal end when the penetrating member is retracted and a safety probe retracted position exposing the penetrating member distal end when the penetrating member is extended, retracting means for moving the penetrating member from the penetrating member extended position to the penetrating member retracted position, means for manually moving the penetrating member from the penetrating member retracted position to the penetrating member extended position, locking means for locking the penetrating member in the penetrating member extended position and preventing proximal movement of the penetrating member during penetration of the anatomical cavity wall, and releasing means responsive to penetration of the safety penetrating instrument into the anatomical cavity for triggering release of the locking means to permit the retracting means to move the penetrating member proximally to the penetrating member retracted position.

Yet another aspect of the present invention is generally characterized in a safety penetrating instrument for establishing a portal in the wall of an anatomical cavity including a housing, a distally-biased portal sleeve movable relative to the housing between an extended rest position and a proximally spaced retracted position, a penetrating member disposed within the portal sleeve and movable relative to the portal sleeve between an extended position where a distal end of the penetrating member protrudes distally from a distal end of the portal sleeve and a retracted position proximally spaced from the extended position, a distally-biased safety probe disposed within the penetrating member and movable relative to the penetrating member between an extended safety probe rest position protecting the penetrating member distal end when the penetrating member is retracted and a safety probe retracted position exposing the penetrating member distal end when the penetrating member is extended, retracting means for moving the penetrating member from the penetrating member extended position to the penetrating member retracted position, means for manually moving the penetrating member from the penetrating member retracted position to the penetrating member extended position, locking means for locking the penetrating member in the penetrating member extended position while permitting a predetermined amount of proximal movement of the penetrating member during penetration of the anatomical cavity wall, penetrating member bias means for biasing the penetrating member distally in the locked penetrating member extended position to permit the penetrating member to move proximally during penetration of the anatomical cavity wall and distally upon introduction into the anatomical cavity, and releasing means responsive to penetration of the safety penetrating instrument into the anatomical cavity for triggering release of the locking means to permit the penetrating member retracting means to move the penetrating member proximally to the penetrating member retracted position.

A further aspect of the present invention is generally characterized in a safety penetrating instrument for establishing a portal in the wall of an anatomical cavity including a housing, a portal sleeve having a proximal end mounted by the housing, a hollow penetrating member disposed within the portal sleeve and having a tissue penetrating distal end with a partially conical configuration having partial threads, and a distally-biased safety probe disposed within the penetrating member and having a distal end with a partially conical configuration having partial threads such that, when the safety probe is in a retracted position relative to the penetrating member, the configuration of the safety probe distal end cooperates with the configuration of the penetrating member distal end to produce a substantially complete geometric cone configuration with external threads.

Other objects and advantages of the present invention will become apparent from the following description of the preferred embodiments taken in conjunction with the accompanying drawings wherein, unless specified otherwise, like parts or parts that perform like functions are identified in each of the several figures by the same reference numeral or by reference numerals sharing the same last two digits.

DESCRIPTION OF THE PREFERRED EMBODIMENTS

Figure 1:
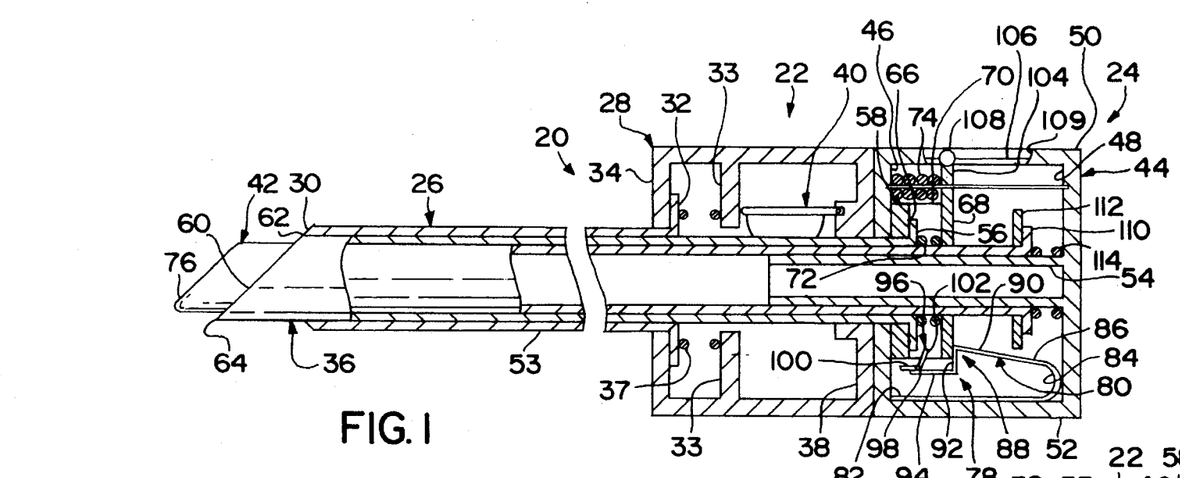
FIG. 1 is a broken side view, partly in section, of a safety penetrating instrument according to the present invention.

A safety penetrating instrument 20 according to the present invention, as shown in FIG. 1, includes a portal unit 22 and a penetrating unit 24. The portal unit 22 includes an elongate portal sleeve 26 and a housing 28 mounting a proximal end of portal sleeve 26. Portal sleeve 26 terminates distally at a distal end 30 and proximally at a flange 32 disposed between a front wall 34 and an inner wall or partition 33 of the housing 28. The portal sleeve 26 can have any desirable cross-sectional configuration, including cylindrical or tubular configurations, in accordance with the procedure to be performed and the anatomical cavity to be penetrated. Preferably, portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member 36 of penetrating unit 24. A bias member 37 is connected between inner wall 33 and flange 32 to bias the portal sleeve in a distal direction. Bias member 37 is shown as a helical coil spring disposed around the penetrating member 36 and held in compression between inner wall 33 and portal sleeve flange 32; however, bias member 37 can include various other types of springs as well as other types of bias devices including compression springs, tension springs, torsion springs, pan springs, leaf springs, rubber, plastic or magnets, for example.

Housing 28 can be made of any desirable material and can have any desirable configuration to facilitate grasping by a surgeon and includes a rear wall 38 having an opening therein aligned with an opening in the housing front wall 34 to allow passage therethrough by the penetrating member 36. The housing 28 is preferably constructed to sealingly engage instruments passing therethrough and to include a valve biased to a closed state when no instrument passes through the portal sleeve. A flapper valve 40 is shown; however, any suitable valve construction can be utilized, including trumpet or nipple valves.

Penetrating unit 24 includes an elongate, hollow penetrating member 36 in the form of a tubular needle, a safety probe 42 and a hub 44 mounting proximal ends of the penetrating member and the safety probe. Hub 44 includes longitudinally spaced front and rear walls 46 and 48 and laterally spaced top and bottom walls 50 and 52. Hub front wall 46 has a configuration to mate with the rear wall 38 of the housing; and, when the hub is mated with the housing as shown, penetrating member 36 is disposed within portal sleeve 26. Penetrating member 36 has an elongate tubular body 53 telescopically fitted over safety probe 42 which is, in turn, telescopically fitted over a guide tube 54 extending distally from hub rear wall 48. The penetrating member terminates proximally at a transverse flange 56 mounted by a rail member 58 in hub 44 and has a beveled distal end 60 that extends from a transverse dimensional transition or junction 62 to define a sharp, tissue-penetrating distal tip 64.

Rail member 58 is generally U-shaped including a forward wall 66 disposed transverse or perpendicular to a longitudinal axis of the penetrating instrument, a rearward wall 68 in configuration parallel to forward wall 66 and a side wall 70 transversely joining the forward and rearward rail member walls. Flange 56 is disposed between the rail member forward and rearward walls with the rail member forward wall 66 having an opening therein allowing passage therethrough by the penetrating member 36. The rail member forward and rearward walls are disposed parallel or substantially parallel to flange 56, and a bias member 72 is connected between penetrating member flange 56 and the rail member rearward wall 68 to bias the penetrating member distally. As shown, bias member 72 includes a helical coil spring disposed around the safety probe 42 and mounted in compression between flange 56 and the rail member rearward wall 68 to bias the penetrating member 36 distally to cause flange 56 to abut the rail member forward wall 66. However, bias member 72 can include various other types of springs as well as other types of bias devices including compression springs, tension springs, torsion springs, pan springs, leaf springs, rubber, plastic or magnets, for example.

A retracting member 74 is mounted between rail member rearward wall 68 and the front wall 46 of hub 44 to bias the penetrating member 36 in a proximal direction to a retracted position where the sharp distal tip 64 of the penetrating member is disposed proximally of the portal sleeve distal end 30 and the safety probe distal end 76 as will be explained further below. The retracting member 74 includes a helical coil spring disposed around a guide rod 75 and mounted in compression between the rail member rearward wall 68 and the hub front wall 46 to bias the rail member 58 and, therefore, the penetrating member 36, in a proximal direction to the retracted position where the distal end 60 of the penetrating member is disposed proximally of the distal end 76 of the safety probe 42 and the portal sleeve distal end 30.

A locking and releasing mechanism 78 for locking the penetrating member in an extended position, shown in FIG. 1, and for releasing the rail member 58 to allow the penetrating member 36 to move to the retracted position includes a latch or locking spring 80, made of a strip of resilient material, formed to have a substantially flat base 82 secured to the bottom wall 52 of hub 44 and a bend 84 joining the proximal end of the base 82 with an upwardly angled arm 86 spaced from the base. Arm 86 carries or forms a latch 88 having a proximal angled latching surface 90 joining a distal latching surface 92 disposed substantially transverse to the longitudinal axis of the safety penetrating instrument and substantially parallel to the rail member rearward wall 68. Arm 86 has an extension 94 positioned distally of latch 88, and a releasing member or trigger 96 is juxtaposed with extension 94. The trigger 96 is pivotally mounted in the hub on a pin 98 secured to a wall or walls of the hub or structure supported in the hub, and the trigger is generally L-shaped with a leg 100 overlying extension 94 and a leg 102 extending transversely from leg 100 but at a slight angle toward the proximal end of the safety penetrating instrument. A torsion spring (not shown) is coiled around pin 98 and fixed to trigger 96 to bias the trigger counterclockwise, looking at FIG. 1, such that leg 100 is biased toward extension 94.

The rail member rearward wall 68 extends toward the top wall 50 of the hub and a post 104 extends from the penetrating member flange through a longitudinal slot 106 formed in the top wall of the hub to terminate at a handle 108 disposed within an elongate trough-like recess 109. Handle 108, which can be coupled with the penetrating member directly or via the rail member as shown, can be grasped and manually moved distally along the slot formed in the top wall of the hub to move the penetrating member from the retracted position to the locked extended position as previously explained above.

Safety probe 42 extends from distal end 76 to a proximal flange 110 disposed between the hub rear wall 48 and an inner wall or partition 112 distally spaced from the hub rear wall. A bias member 114 in the form of a helical coil spring is disposed around the guide tube 54 and held in compression between the safety probe flange 110 and the hub rear wall 48 to bias the safety probe 42 distally toward a rest position where the safety probe flange abuts the hub partition 112. Distal end 76 of the safety probe is relatively blunt and is beveled at substantially the same angle as penetrating member distal end 60 so that when the safety probe is moved proximally relative to the penetrating member, the distal ends of the probe and the penetrating member can become aligned or flush to form a substantially solid geometric configuration easing penetration.

The portal unit 22 and the penetrating unit 24 can be provided separately or assembled together as shown in FIG. 1, and either or both of the portal and penetrating units can be manufactured in a manner to be disposable for single patient use or to be sterilizable for re-use. The hub 44 can be coupled to the housing 28 by suitable detent or latch mechanisms if desired, and the penetrating unit can be withdrawn from the portal unit leaving the portal sleeve 26 in place within an anatomical cavity to serve as a portal for the introduction of medical instruments therethrough.

Figure 3:
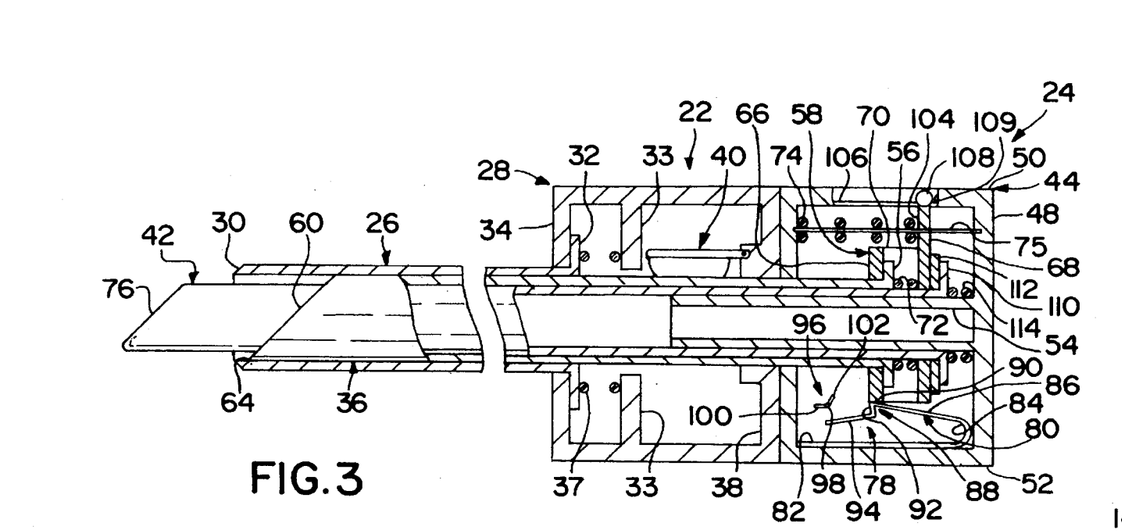
FIG. 3 is a broken side view, partly in section, of the safety penetrating instrument of FIG. 1 following penetration into the anatomical cavity.

In use, the safety penetrating instrument 20 is preferably provided in the condition illustrated in FIG. 3 with the safety probe 42 in the extended rest position and the penetrating member 42 in the retracted position such that the distal end 60 of the penetrating member is proximally spaced from the distal end 76 of the safety probe to protect the sharp tip 64 of the penetrating member prior to use. In order to move the penetrating member to the extended position shown in FIG. 1, the handle 108 is grasped to move the rail member 58, and thus the penetrating member 36, distally until the rail member rearward wall 68 rides over latch 88 to be latched in the extended position with the rail member rearward wall 68 locked against distal latching surface 92. The user can feel the rail member rearward wall 68 lock into place in engagement with the latch 88 and can also visually determine that the penetrating member is in the locked extended position by noting the position of the handle 108 at a distal end of the slot 106.

Figure 2:
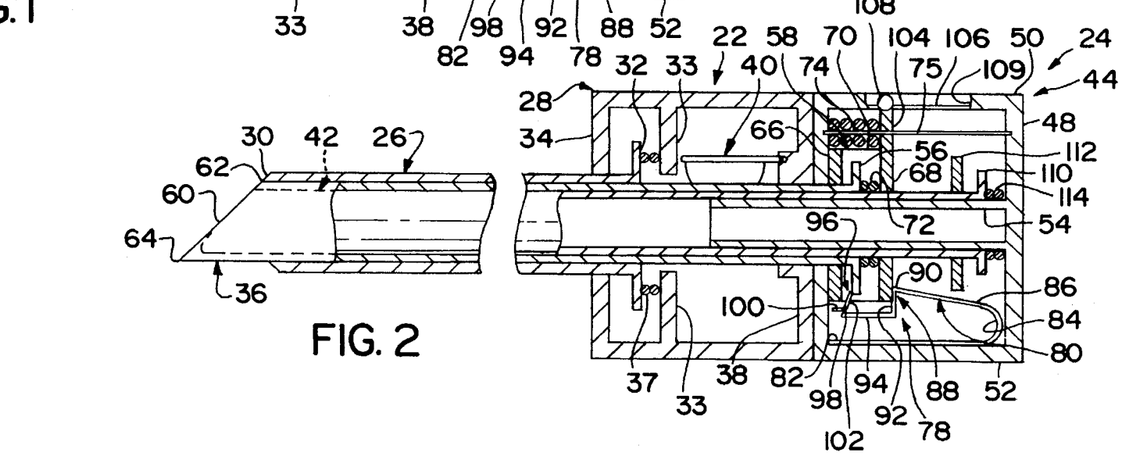
FIG. 2 is a broken side view, partly in section, of the safety penetrating instrument of FIG. 1 during penetration of a wall of an anatomical cavity.

With the penetrating member 36 locked in the extended position illustrated in FIG. 1, the distal end 60 of the penetrating member protrudes distally from the portal sleeve distal end 30 and the safety probe distal end 76 protrudes distally from the distal tip 64 of the penetrating member. Portal sleeve distal end 30 is preferably aligned with junction 62 of the penetrating member 36 to present a smooth distal profile easing penetration; and the portal sleeve 26, penetrating member 36 and safety probe 42 can all move proximally in response to forces acting on their respective distal ends, such as the force from tissue contact during penetration of an anatomical cavity wall. Proximal movement of the portal sleeve 26 is limited by compression of bias member 37 against housing partition 33, which serves as a stop or abutment. Similarly, proximal movement of the penetrating member is limited by compression of bias member 72 against the rearward wall 68 of the rail member, and safety probe 42 can move proximally against the bias of bias member 114 in response to forces acting on the safety probe distal end 76 until bias member 114 is completely compressed against the hub rear wall 48. When penetration of an anatomical cavity wall is commenced, the force from tissue contact on the safety probe distal end 76 will cause the safety probe to move proximally against the bias of bias member 114 so that the beveled distal end 76 of the probe becomes flush with the beveled distal end 60 of the penetrating member to form a substantially solid geometric configuration for penetrating the anatomical cavity wall. Portal sleeve 26, safety probe 42 and penetrating member 36 can all move proximally in response to tissue resistance during penetration, so the alignment of the safety probe and portal sleeve distal ends with the penetrating member distal end can be substantially maintained in order to ease penetration. Penetrating member flange 56 will also move past trigger leg 102 but will not cause movement of latch 88 since clockwise rotation of the trigger does not bring trigger leg 100 into contact with arm extension 94; and, since trigger 96 is biased in a counterclockwise direction, flange 56 will be positioned proximally of trigger leg 102 as shown in FIG. 2.

Upon entry into the anatomical cavity, the counterforce on the safety probe, portal sleeve and penetrating member distal ends caused by tissue contact will be reduced allowing bias members 114, 37 and 72 to move the safety probe, portal sleeve and penetrating member distally. Distal movement of the penetrating member causes flange 56 to operatively engage trigger leg 102 and to pivot the trigger counterclockwise looking at FIG. 2 causing leg 100 to engage arm extension 94. The engagement of leg 100 with arm extension 94 causes arm 86 to move toward base 82 moving the latch 88 out of engagement with the rail member rearward wall 68 thereby allowing the retracting member 74 to cause the penetrating member to move proximally to the retracted position wherein the rail member rearward wall 68 abuts the hub partition 112 and the penetrating member distal end 60 is proximally spaced from the safety probe distal end 76 and the portal sleeve distal end 30 to protect the sharp tip 64 of the penetrating member as shown in FIG. 3. The penetrating unit 24 including the penetrating member 36 and the probe 42 can then be withdrawn from the portal unit 22 leaving the portal sleeve 26 in place within the anatomical cavity wall to serve as a portal for introducing medical instruments therethrough.

Figure 4:
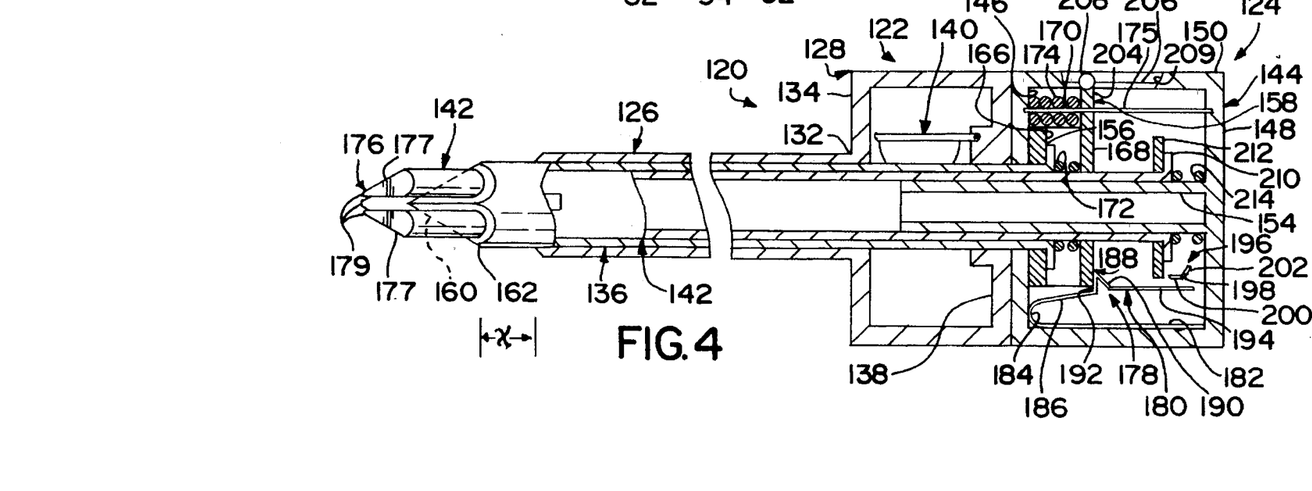
FIG. 4 is a broken side view, partly in section, of a modification of a safety penetrating instrument according to the present invention.

The safety penetrating instrument of the present invention can be modified as shown in FIG. 4 at 120 to permit proximal movement of the penetrating member 136 and probe 142 of the safety penetrating instrument during penetration of an anatomical cavity wall and to trigger movement of the penetrating member 136 to the retracted position in response to distally-biased movement of the safety probe 142 caused by a reduction in force from tissue contact upon entry into the anatomical cavity. The modified safety penetrating instrument 120 includes a penetrating unit 124 similar to penetrating unit 24 for safety penetrating instrument 20 but with a modified locking and releasing mechanism 178 and a hollow penetrating member 136 having a partial geometric configuration of a pyramid at a distal end 160 with sides or facets tapering to a sharp tip 164 while openings at the distal end defined by a peripheral edge terminate at a sharp tip 164. Locking and releasing mechanism 178 includes a locking spring 180 having a flat base 182 secured to a bottom wall 152 of the hub and a bend 184 joining a distal end of the base with an upwardly angled arm 186. Arm 186 turns upward, toward a longitudinal axis of the instrument, to form a latch 188 having a transverse latching surface 192 in configuration parallel to the rail member rearward wall 168. An angled proximal latching surface 190 extends downward from latching surface 192 to connect with a horizontal arm extension 194 extending parallel to the longitudinal axis of the instrument. A trigger 196, similar to trigger 96 for safety penetrating instrument 20, is juxtaposed with arm extension 194 but is spaced proximally from hub partition 112 for being engaged by safety probe flange 210. Trigger 196 is pivotally mounted on a pin 198 secured to a wall or walls of the hub between arm extension 194 and the safety probe flange 210. Trigger 196 is generally L-shaped with a leg 200 overlying extension 194 and a leg 202 extending transversely from leg 200 and toward the proximal end of the hub to be disposed proximally of the safety probe flange 210 when the safety probe is in the extended rest position shown.

Figure 5:
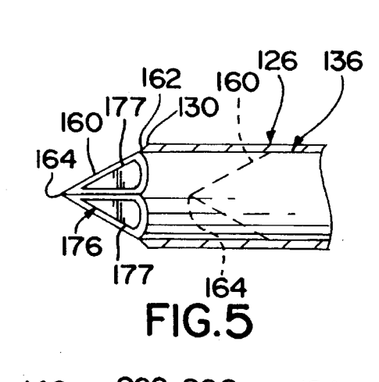
FIG. 5 is a fragmentary side view, partly in section, of the distal end of the safety penetrating instrument of FIG. 4 during penetration of an anatomical cavity wall.

Safety probe 142 is movably disposed concentrically within penetrating member 136 and has an elongate cross-sectional configuration corresponding to that of the hollow penetrating member and a distal end 176 formed of sides or facets 177 tapering to a narrow end 179, the configuration of the distal end cooperating with the configuration of the distal end of the penetrating member, when the safety probe is in the retracted position as illustrated in FIG. 5, to produce a substantially complete geometric pyramid configuration having four sides or facets symmetrically arranged around a sharp point.

Portal unit 122 for safety penetrating instrument 120 includes a tubular portal sleeve 126 having a proximal end 132 fixedly secured to the front wall 134 of a housing 128. Portal sleeve 126 fits telescopically over penetrating member 136 when the penetrating and portal units are assembled as shown in FIG. 4, and a distal end 130 of the portal sleeve is proximally spaced from junction 162 of the penetrating member a predetermined distance x, corresponding approximately to the distance between rail member walls 166 and 168, when the penetrating member is in the extended rest position shown.

Use of the safety penetrating instrument 120 for penetrating an anatomical cavity wall proceeds essentially as described above for safety penetrating instrument 20 with the exception that portal sleeve 126 does not move relative to housing 128 during penetration, and retraction of penetrating member 136 is triggered by distally-biased movement of safety probe 142 upon entering the anatomical cavity. Prior to contacting the anatomical cavity wall, handle 208 is grasped and manually moved distally relative to hub 144 to move rail member 158, and thus penetrating member 136, distally to the locked, extended position shown in FIG. 4 where distal end 160 of the penetrating member protrudes distally from the portal sleeve distal end 130 and distal end 176 of the safety probe protrudes distally from the penetrating member distal end. Upon contacting the anatomical cavity wall, safety probe 142 is moved proximally relative to hub 144 due to the force from tissue contact until distal end 176 of the safety probe is flush with penetrating member distal end 160, after which the safety probe 142 and penetrating member 136 can move together proximally relative to hub 144 while defining a substantially complete geometric pyramid configuration to ease penetration. When bias members 114 and 172 are fully compressed against proximal abutment surfaces defined by the rail member and hub rear walls, respectively, junction 162 of the penetrating member is preferably aligned with portal sleeve distal end 130 to form a smooth distal profile as shown in FIG. 5. Upon penetrating into the anatomical cavity, the counterforce on the distal ends of the penetrating member and safety probe are reduced allowing the respective bias members to move the penetrating member and safety probe distally. As shown, distally-biased movement of the safety probe causes safety probe flange 210 to operatively engage leg 202 of trigger 196 thereby rotating the trigger counter-clockwise and triggering release of the penetrating member from the locked extended position so that the penetrating member can be moved proximally to a retracted position, shown by phantom line in FIG. 5, where the distal end of the penetrating member is proximally spaced from both the portal sleeve and safety probe distal ends.

Figure 6:
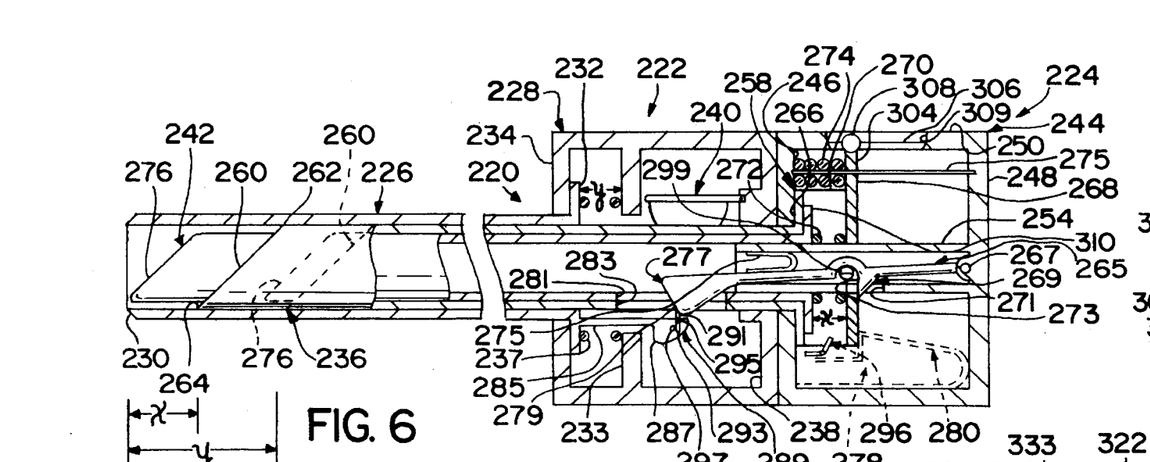
FIG. 6 is a broken side view, partly in section, of another modified safety penetrating instrument according to the present invention.

Still another modification of the safety penetrating instrument according to the present invention is illustrated in FIG. 6 at 220. The modified safety penetrating instrument 220 is similar to safety penetrating instrument 20 with the exception that the penetrating member does not move when locked in the extended position and movement of the penetrating member from the extended position to the retracted position is triggered by distally-biased movement of the portal sleeve in response to a reduction in the force from tissue contact following entry into the anatomical cavity. Safety penetrating instrument 220 includes a portal unit 222 and a penetrating unit 224 having a penetrating member 236, a safety probe 242 and a hub 244 mounting proximal ends of the penetrating member and the safety probe. Penetrating member 236 is similar to penetrating member 36 and includes a beveled distal end 260 and a proximal end 256 fixedly secured to the forward wall 266 of a rail member 258. Safety probe 242 is similar to safety probe 42 and is telescopically fitted within penetrating member 236; however, flange 310 at the proximal end of safety probe 242 is mounted between forward and rearward walls 266 and 268 of rail member 258 and a bias member 272 is disposed around the guide tube 254 and held in compression between the safety probe flange 310 and the rearward wall of rail member 258 to bias the safety probe distally to a rest position where the safety probe flange abuts the forward wall of the rail member. A retracting member 274, similar to retracting member 74, is held in compression between the forward wall 246 of the hub and the rearward wall 268 of the rail member to bias the rail member, and thus the penetrating member and safety probe, in a proximal direction toward a retracted position.

Rail member 258 is locked in the extended position shown in FIG. 6 by a longitudinal latch arm 265 disposed within the guide tube 254 and having a proximal end pivotally mounted on a pin 267 secured to the rear wall 248 of the hub. Latch arm 265 carries a latching protrusion 269 in opposed relation to a slot 271 formed in the guide tube 254. Protrusion 269 is generally triangular with a transverse latching surface 273 configured to extend through slot 271 and to engage the rail member rearward wall 268. A leaf spring 275 is connected between the latch arm 265 and an inner surface of the guide tube 254 to bias the arm 265 in a counterclockwise direction looking at FIG. 6 toward an engaged position where latching protrusion 269 extends through the slot 271 formed in the guide tube. A triggering protrusion 277 is formed at a distal end of the latch arm 265 and includes a distal edge 279 that protrudes through aligned slots 281 and 283 formed in the safety probe 242 and the penetrating member 236 distally of slot 271 to communicate into housing 228. Slots 281 and 283 are sufficiently long to allow back and forth movement of the safety probe and penetrating member between extended and retracted positions within the hub.

Portal unit 222 is similar to portal unit 22 for safety penetrating instrument 20 and, in addition, includes a finger 285 extending perpendicularly from the portal sleeve flange 232 in a proximal direction to terminate proximally at an enlarged head 287. A lever 289 having axially opposed ends 291 and 293 is pivotally mounted on a pin 295 secured to head 287. A peg 297 extends from head 287 and is proximally spaced from lower end 293 of lever 289 to serve as a stop limiting clockwise rotation of the lever beyond a position where upper end 291 extends transversely from finger 285 in a manner to engage triggering protrusion 277 when finger 285 is moved. A torsion spring (not shown) is mounted between the lever and the head to normally bias the lever into abutting relation with peg 297. Also shown in FIG. 6 is a tapered control button 299 in the form of a wedge that extends transversely alongside latch arm 265 for manually disengaging the latch arm from the rail member by rotating the latch arm clockwise when depressed or driven through the hub.

Use of the safety penetrating instrument 220 is similar to that described above with respect to safety penetrating instrument 20 in that, when the user desires to penetrate into an anatomical cavity, the safety penetrating instrument will normally be provided with the penetrating member 236 in the retracted position where the distal end 260 of the penetrating member is proximally spaced from the portal sleeve distal end 230 and the safety probe distal end 276. Additionally, the portal sleeve 226 and safety probe 242 will be provided in rest positions where the portal sleeve flange 232 abuts the housing front wall 234 and the safety probe flange 310 abuts the rail member forward wall 266. Furthermore, latching protrusion 269 of latch arm 265 will be disposed distally of the rail member rearward wall 268 and upper end 291 of lever 289 will be disposed distally of latching protrusion 277. The penetrating member 236 is biased to the retracted position by retracting member 274 with handle 308 being disposed at a proximal end of slot 306 in hub 244.

Prior to commencing penetration of an anatomical cavity wall, handle 308 is grasped and manually moved distally to move penetrating member 236 distally against the bias of retracting member 274 until the rail member rearward wall 268 rides over the latching protrusion 269 by engaging an angled proximal surface of the latching protrusion 269 to move the latch arm 265 clockwise looking at FIG. 6. When rail member rearward wall 268 moves distally past latching surface 273, latch arm 265 springs back in a counter-clockwise direction to lock the rail member 258 and penetrating member 236 mounted thereby in the extended position shown. As previously noted, the user can feel the rail member lock into place in engagement with latch arm 265 and can also visually determine that the penetrating member is in the locked extended position by noting the position of the handle 308 at a distal end of the slot. With the penetrating member 236 locked in the extended position, safety probe flange 310 will be distally biased by bias member 272 into abutting relation with the rail member forward wall 266 such that the safety probe distal end 276 is axially spaced from penetrating member distal end 260 a predetermined distance x approximately equal to the spacing between rail member walls 266 and 268. Also, the portal sleeve flange 232 will be distally biased by bias member 237 into abutment with housing forward wall 234 such that the distal end 230 of the portal sleeve will be distally spaced from the penetrating member junction 262 a predetermined distance y approximately equal to the distance between the housing front wall 234 and partition 233.

With the safety penetrating instrument 220 in the position illustrated in FIG. 6, penetration of the anatomical cavity wall is commenced, and the force from tissue contact on the portal sleeve and safety probe distal ends 230 and 276 will cause the portal sleeve and safety probe to move together proximally against the bias of springs 237 and 272, respectively. Proximal movement of the portal sleeve 226 also causes upper end 291 of lever 289 to contact and move past triggering protrusion 277 by rotating counter-clockwise underneath the protrusion. When lever upper end 291 clears protrusion 277 lever 289 rotates in a clockwise direction; and, accordingly, lever upper end 291 will then be positioned proximally of triggering protrusion 277. Upon entry into the anatomical cavity, the counterforce on the distal end of the portal sleeve will be reduced allowing spring 237 to move the portal sleeve distally causing lever upper end 291 to engage triggering protrusion 277 and thereby to pivot the lever 289 clockwise causing lever lower end 293 to engage peg 297 preventing further clockwise rotation of lever 289. The engagement of lever 287 with triggering protrusion 277 causes latch arm 265 to rotate clockwise, looking at FIG. 6, moving the latching protrusion 269 out of engagement with rail member rearward wall 268 thereby allowing retracting member 274 to cause the penetrating member to move proximally to the retracted position, shown by phantom line in FIG. 6, wherein the penetrating member distal end 260 is proximally spaced from the distal end 230 of the portal sleeve 226 to protect the sharp tip 264 of the penetrating member. The penetrating unit 224 can then be withdrawn from the portal unit 222 leaving the portal sleeve 226 in place for the introduction of medical instruments therethrough.

Another modification of the safety penetrating instrument of the present invention is arrived at by combining the locking and releasing mechanisms of safety penetrating instruments 20 and 220 to permit movement of the penetrating member to the retracted position in response to distally-biased movement of both the portal sleeve and the safety probe. The modification involves mounting a locking and releasing mechanism such as locking and releasing mechanism 78 for engaging the rail member 258 in hub 244 of safety penetrating instrument 220 as shown in phantom at 278 in FIG. 6. Use of the modified safety penetrating instrument is similar to that described above in connection with safety penetrating instruments 20 and 220 with the exception that safety probe flange 310 serves as an operating member for engaging trigger 296 of the locking and releasing mechanism 278 and both the latch spring 280 and latch arm 265 must be disengaged in order for the penetrating member 236 to be moved proximally to the retracted position.

Figure 7:
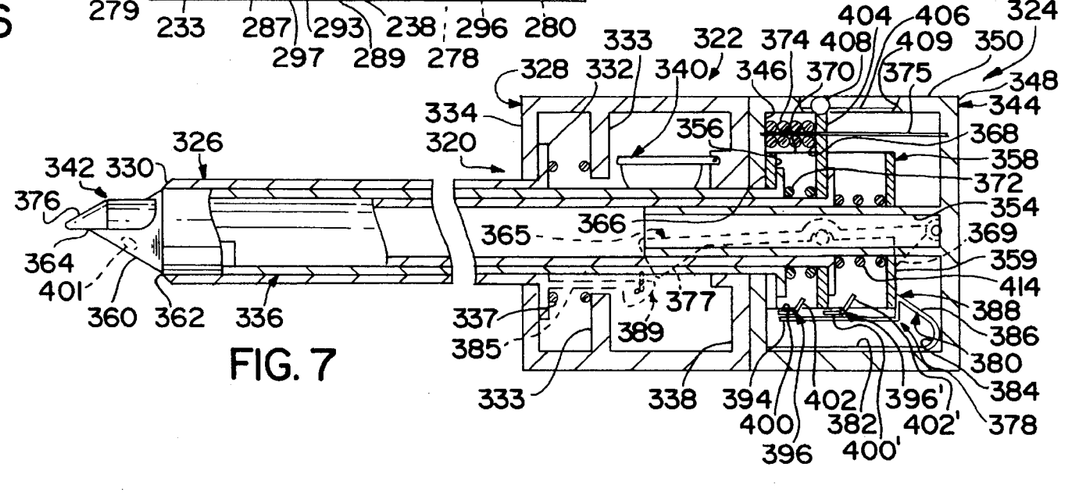
FIG. 7 is a broken side view, partly in section, of still another modified safety penetrating instrument according to the present invention.

FIG. 7 illustrates a further modification of the safety penetrating instrument of the present invention wherein the portal sleeve 326, penetrating member 336 and safety probe 342 of the modified safety penetrating instrument 320 are movable in a proximal direction during penetration, and movement of the penetrating member from the extended position to the retracted position is triggered by distally-biased movement of one or both of the penetrating member and safety probe upon entering the anatomical cavity. Safety penetrating instrument 320 includes a portal unit 322 identical to portal unit 22 and a penetrating unit 324 including a hub 344, a modified rail member 358 mounting proximal ends of penetrating member 336 and safety probe 342, and a modified locking and releasing mechanism 378. Penetrating member 336 is hollow, and a distal end 360 of penetrating member 336 has a partially conical configuration terminating at a sharp tissue penetrating tip 364. Safety probe 342 has an elongate circular configuration in cross-section corresponding to the tubular configuration of the penetrating member and a distal end 376 having a partially conical configuration corresponding to the configuration of the distal end 360 of penetrating member 336 such that, when the safety probe is in the retracted position illustrated in FIG. 8, the configuration of the safety probe distal end cooperates with the configuration of the distal end of the penetrating member to produce a substantially complete geometric cone configuration.

Rail member 358 is similar to rail member 58 except that side wall 370 of rail member 358 extends proximally beyond rearward wall 368 to connect with an additional wall 359 having a configuration parallel to walls 366 and 368. Penetrating member flange 356 is disposed between the rail member forward and rearward walls with the rail member forward wall 366 having an opening therein allowing passage therethrough by the penetrating member 36. Safety probe flange 410 is disposed between rail member walls 368 and 359 with wall 368 having an opening formed therein allowing passage of the safety probe therethrough and wall 359 having an opening formed therein allowing passage of guide tube 354. The rail member forward and rearward walls are disposed parallel or substantially parallel to penetrating member flange 356, and a bias member 372 is connected between penetrating member flange 356 and the rail member rearward wall 368 to bias the penetrating member distally. Similarly, rail member walls 368 and 359 are disposed parallel or substantially parallel to safety probe flange 410, and a bias member 414 is connected between safety probe flange 410 and the additional wall 359 to bias the safety probe distally.

Figure 8:
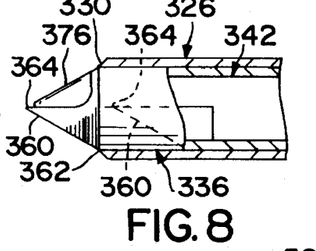
FIG. 8 is a fragmentary side view, partly in section, of the distal end of the safety penetrating instrument of FIG. 7 during penetration of an anatomical cavity wall.

Retracting member 374 is mounted between rail member rearward wall 368 and the front wall 346 of hub 344 to bias the rail member 358, and thus the penetrating member 336 and safety probe 342, in a proximal direction to a retracted position where the sharp distal tip 64 of the penetrating member is disposed proximally of the portal sleeve distal end 330 as shown by phantom line in FIG. 8. Locking and releasing mechanism 378 for safety penetrating instrument 320 is similar to locking and releasing mechanism 78 but with latch 388 engaging the additional wall 359 to lock the rail member in the extended position shown in FIG. 7 and a pair of spaced triggers 396 and 396' juxtaposed with arm extension 394. Trigger 396 is identical to trigger 396 and includes a leg 400 overlying extension 394 and a leg 402 extending transversely from leg 400 toward the proximal end of the instrument to be disposed proximally of penetrating member flange 356 when the penetrating member flange abuts the rail member forward wall 366. Trigger 396' is similar to trigger 396 but is proximally spaced so that a leg 400' overlies extension 394 and a leg 402' extends transversely from leg 400' toward the proximal end of the instrument to be disposed proximally of safety probe flange 410 when the safety probe flange abuts the rail member rearward wall 368.

Safety penetrating instrument 320 operates similar to safety penetrating instrument 20 with the exception of both penetrating member and safety probe flanges serving as operating members for operatively engaging triggers overlying the arm extension. Therefore, once the safety penetrating instrument has entered an anatomical cavity, distally-biased movement of either or both the penetrating member and the safety probe can trigger release of the penetrating member to be moved proximally to the retracted position.

Another modification of the safety penetrating instrument of the present invention is arrived at by combining the locking and releasing mechanisms of safety penetrating instruments 320 and 220 to permit movement of the penetrating member to the retracted position in response to distally-biased movement of the portal sleeve 326 and one or both of the penetrating member 336 and safety probe 342. The modification, shown by phantom line in FIG. 7, involves positioning a latch arm 365, similar to latch arm 265, inside guide tube 354 of hub 344 for engaging the additional wall 259 of rail member 258 of safety penetrating instrument 320 to lock the rail member in the extended position and mounting a finger 385 with an enlarged head 387 and a lever 389 on portal sleeve flange 332 for operatively engaging a triggering protrusion 377 of the latch arm to release the rail member in response to distally-biased movement of the portal sleeve. Use of the modified safety penetrating instrument is similar to that described above in connection with safety penetrating instruments 320 and 220 with the exception that both the latch spring 380 and latch arm 365 must be disengaged in order for the penetrating member 236 to be moved proximally to the retracted position.

From the above, it will be appreciated that multiple penetrating components of the safety penetrating instrument of the present invention are movable proximally during penetration of an anatomical cavity wall and are biased to move distally upon entering the anatomical cavity. By "penetrating components" is meant those elements of the safety penetrating instrument that enter an anatomical cavity, such as the portal sleeve, safety probe and penetrating member of the safety penetrating instrument; and retraction of the penetrating member to a position where the distal end of the penetrating member is protected can be conditioned upon distally-biased movement of one or more of the penetrating components, such as the portal sleeve, the safety probe and/or the penetrating member, depending on the type and number of locking and releasing mechanisms provided. Furthermore, distal ends of the portal sleeve, the safety probe and/or the penetrating member can be aligned prior to penetration to define a substantially complete solid geometric configuration having a smooth distal profile for penetrating anatomical tissue, and the distal configuration can be substantially maintained during penetration by permitting proximal movement of the penetrating member, portal sleeve and/or safety probe. Alternatively, the distal ends of the portal sleeve and/or the safety probe can be distally or proximally spaced from the penetrating member distal end such that movement of the portal sleeve, safety probe and/or penetrating member in response to tissue contact will cause the distal ends of the portal sleeve, safety probe and penetrating member to become aligned and to define a substantially complete solid geometric configuration. If the portal sleeve and/or safety probe distal ends are distally spaced from the penetrating member distal end in the extended rest position, the portal sleeve and/or safety probe will also function as safety members to protect the penetrating member distal end in the event that the penetrating member is not retracted.

The components of the safety penetrating instrument of the present invention can be made of any suitable, medical grade materials to permit sterilization for re-use or for single patient use. The components can be made of multiple parts of various configurations and materials to reduce cost. The portal unit and/or penetrating unit can have various valves, stop cocks and seals mounted thereon to control fluid flow therethrough, and conventional detent mechanisms can be used to connect or latch the hub with the housing when the portal unit and the penetrating unit are assembled. The distal end of the portal sleeve can be chamfered or blunt, smooth or roughened, or have any other configuration depending on the need for ease of penetration or increased resistance. Also, the strength of the bias members biasing the portal sleeve, safety probe and/or penetrating member can be chosen according to differences in the resistant forces acting on the portal sleeve, safety probe and penetrating member in order to maintain a smooth distal profile during penetration.

Any of the penetrating members shown and described herein can include a viewing port, like the viewing port shown in phantom at 401 in FIG. 7, for accommodating conventional optical viewing systems such as those utilizing fiber optics so that tissue can be visualized during penetration.

In any safety penetrating instrument having a penetrating member that can move while locked in the extended position, the safety probe distal end can be configured to normally protrude distally from the penetrating member distal end as shown or to line up or cooperate with the distal end of the penetrating member to define a substantially complete solid geometric configuration suitable for penetrating anatomical tissue. In the latter case, the safety probe will preferably protrude distally from the penetrating member when the penetrating member is retracted so that the tip of the penetrating member is protected when the unit is removed from the portal unit.

Figure 9:
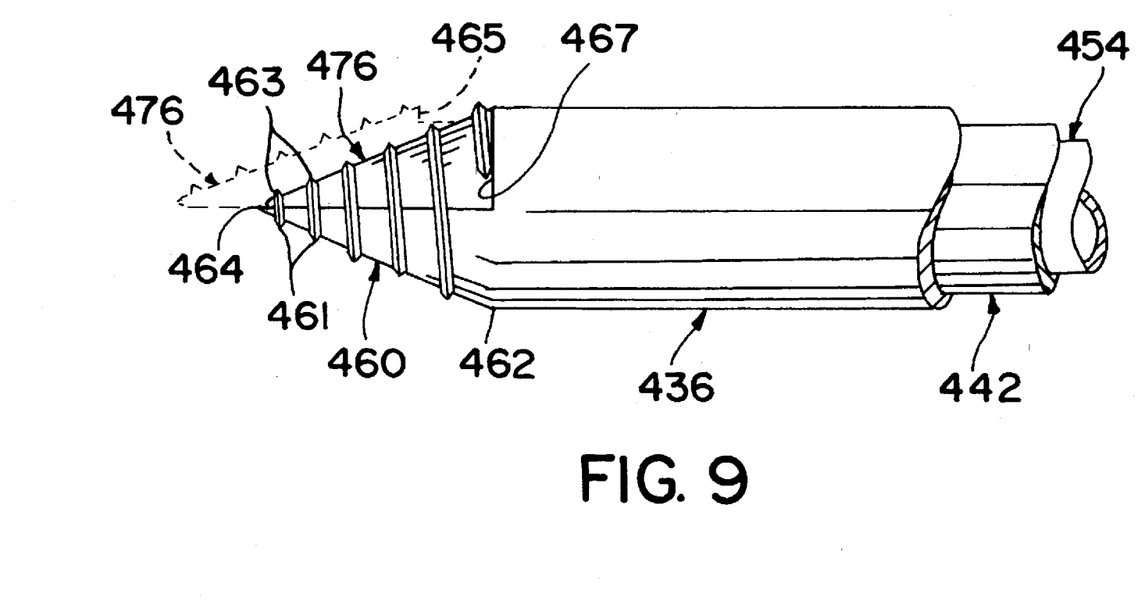
FIG. 9 is a fragmentary side view of a modified distal end configuration for a safety penetrating instrument according to the present invention.

The penetrating member and safety probe of the safety penetrating instrument can have any distal configuration to define a substantially complete geometric configuration when aligned such as, for example, the distal configurations shown and described in my copending patent application Ser. No. 08/178,153, filed Jan. 6, 1994, the disclosure of which is incorporated herein by reference. FIG. 9 shows another distal end configuration wherein the modified penetrating member 436 has a distal end 460 with a partially conical configuration and partially helical threads 461. Safety probe 442 has an elongate portion of circular configuration in cross-section to fit within the penetrating member and a distal end 476 having a partially conical configuration with partially helical threads 463 corresponding to the configuration of distal end 460 of penetrating member 436. As shown by phantom line in FIG. 9, safety probe 442 can be biased such that distal end 476 of the safety probe protrudes distally from penetrating member distal end 460 when the safety probe and penetrating member are in extended rest positions. Alternatively, safety probe distal end 476 can be normally aligned with penetrating member distal end 460 when the safety probe and penetrating member are in extended rest positions. If safety probe 442 is distally-biased to protrude from penetrating member 436, contact with anatomical tissue will cause the safety probe to move proximally relative to the penetrating member until a shoulder 465 formed at the junction of the partially conical and elongate safety probe portions abuts a peripheral edge 467 of an opening formed at the penetrating member distal end through which the safety probe protrudes. When safety probe 442 is in the retracted position shown by solid line in FIG. 9, the configuration of the safety probe distal end cooperates with the configuration of the penetrating member distal end to produce a substantially complete geometric cone configuration with external threads, such that penetration of an anatomical cavity wall can be accomplished by screwing the tip of the safety penetrating instrument through the wall with a minimum of pushing to provide an added element of safety. Upon penetrating into the anatomical cavity, the safety probe can be distally-biased to protrude and/or the penetrating member can be retracted to protect the tissue penetrating tip 464 of the penetrating member.

The rail member can have various configurations to engage the latch and be released by the trigger. Preferably, the rail member will have a configuration to serve as a stop or abutment for the penetrating member and/or safety probe as exemplified herein by a U-shaped rail member. The locking and releasing mechanisms require only a latch for locking the penetrating member in the extended position and a trigger for releasing the latch in response to distal movement of an operating member such as a flange carried by the penetrating member, safety probe and/or portal sleeve; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in U.S. Pat. Nos. 5,330,432; 5,324,268; 5,320,610; 5,336,176; and 5,360,405 to Yoon and pending applications Ser. No. 07/848,838, filed Mar. 10, 1992; Ser. No. 07/845,177, filed Sep. 15, 1992; Ser. No. 07/945,177, filed Sep. 15, 1992; Ser. No. 08/079,586, filed Jun. 22, 1993; Ser. No. 08/195,512, filed Feb. 14, 1994; Ser. No. 08/196,029, filed Feb. 14, 1994; Ser. No. 08/196,027, filed Feb. 14, 1994; Ser. No. 08/195,178, filed Feb. 14, 1994; Ser. No. 08/237,734, filed May 4, 1994; Ser. No. 08/247,205, filed May 20, 1994; Ser. No. 08/254,007, filed Jun. 3, 1994; and Ser. No. 08/260,439, filed Jun. 15, 1994. The disclosures of the above-listed issued patents and pending patent applications are incorporated herein by reference. The issued patents and pending applications listed above also disclose various bias arrangements useful with the safety penetrating instrument of the present invention. Other locking and releasing mechanisms that can be used in the safety penetrating instrument of the present invention are disclosed in Applicant's pending applications Ser. Nos. 08/279,170 and 08/279,172, filed Jul. 22, 1994, the disclosures of which are incorporated herein by reference.

Latch arms, such as latch arms 265 and 365, and fingers, such as fingers 285 and 385, can be incorporated in any safety penetrating instrument having a movable portal sleeve to condition retraction of the penetrating member on distally-biased movement of the portal sleeve for added safety. For example, safety penetrating instrument 20 can be modified by positioning a latch arm within guide tube 54 and mounting a finger on portal sleeve 32 so that retraction of penetrating member 36 is conditioned on distally-biased movement of both the portal sleeve and the penetrating member upon entering an anatomical cavity. Similarly, penetrating unit 124 of safety penetrating instrument 120 can be modified to carry a latch arm and can be mated with a portal unit like portal unit 222 so that retraction of the penetrating member 136 is conditioned on distally-biased movement of the portal sleeve and the safety probe. When a latch arm, such as latch arm 265, is disposed within a hollow portion of a safety probe and/or a guide tube for engaging the rail member of a safety penetrating instrument, the latch arm can be pivotally mounted at a proximal end to the hub as shown or mounted within the guide tube for pivotal movement about a center of the arm or about any other portion of the arm. In addition, such a latch arm can be embodied in a spring strip held in compression within the guide tube and configured to form or carry latching and triggering protrusions. Furthermore, when latch arms are disposed within the safety probe or a guide tube, operating members can be carried by the penetrating member, safety probe and/or portal sleeve on inside surfaces thereof for engaging triggering portions of the latch arms within the penetrating members to release latching portions of the latch arms holding the penetrating members in their extended positions. Latch arms having such features are shown and described in my copending applications Ser. Nos. 08/279,170 and 08/279,172, filed Jul. 22, 1994.

One or more control buttons, such as control button 299 or any button described in my copending patent application Ser. No. 08/083,220, filed Jun. 24, 1993, can be mounted next to any latch for manually disengaging the latch to prevent locking of the penetrating member in the extended position. Furthermore, additional latches can be provided or existing latches modified to carry pawls or form latching surfaces for locking a penetrating member in the retracted position and/or a safety member in an extended position for added safety.

It will also be appreciated that after penetration of the safety penetrating instrument into the anatomical cavity, the distally-biased portal sleeve and/or safety probe can act as a shock absorber upon inadvertent contact with tissue. The distal bias for the triggering member (i.e., the portal sleeve, safety probe and/or penetrating member) of the safety penetrating instrument need only be strong enough to allow slight movement of the member during penetration such that the force-to-penetrate can be minimized.

The features of the various embodiments described above can be combined in any manner desired dependent upon the operational requirements and complexity of the safety penetrating instrument. For example, portal unit 122 can be coupled with penetrating units 24 and 324 when movement of the portal sleeve relative to the housing is contraindicated, and portal unit 22 or 322 can be coupled with penetrating unit 124 when movement of the portal sleeve relative to the housing is desired.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity comprising a housing;

an elongate portal sleeve having a proximal end mounted by said housing and a distal end for introduction in the anatomical cavity;

a hollow penetrating member disposed within said portal sleeve and having a distal end for penetrating the anatomical cavity wall, said penetrating member being movable relative to said portal sleeve between an extended position where said distal end of said penetrating member protrudes distally from said distal end of said portal sleeve and a retracted position proximally spaced from said extended position;

a safety probe disposed within said penetrating member, said safety probe being movable relative to said portal sleeve between an extended safety probe rest position protecting said penetrating member distal end when said penetrating member is retracted and a safety probe retracted position exposing said penetrating member distal end when said penetrating member is extended;

safety probe bias means for biasing said safety probe distally toward said safety probe rest position;

retracting means for moving said penetrating member from said penetrating member extended position to said penetrating member retracted position;

means for manually moving said penetrating member from said penetrating member retracted position to said penetrating member extended position;

locking means for locking said penetrating member in said penetrating member extended position while permitting a predetermined amount of proximal movement of said penetrating member during penetration of the anatomical cavity wall;

penetrating member bias means for biasing said penetrating member distally in said locked penetrating member extended position to permit said penetrating member to move proximally during penetration of the anatomical cavity wall and distally upon introduction into the anatomical cavity; and releasing means responsive to penetration of said safety penetrating instrument into the anatomical cavity for triggering release of said locking means to permit said retracting means to move said penetrating member to said penetrating member retracted position.

2. A safety penetrating instrument as recited in claim 1 wherein said releasing means is responsive to distally-biased movement of said penetrating member upon penetrating into the anatomical cavity.

3. A safety penetrating instrument as recited in claim 2 and further comprising a rail member mounting a proximal end of said penetrating member, wherein said proximal end of said penetrating member includes a flange movable within said rail member and said locking and releasing mechanism includes a latch spring engaging said rail member to lock said penetrating member in said extended position and a trigger responsive to distally-biased movement of said penetrating member flange for releasing said latch spring.

4. A safety penetrating instrument as recited in claim 1 wherein said releasing means is responsive to distally-biased movement of said safety probe upon penetrating into the anatomical cavity.

5. A safety penetrating instrument as recited in claim 4 and further comprising a rail member mounting a proximal end of said penetrating member, wherein said proximal end of said penetrating member includes a flange movable within said rail member and said locking and releasing mechanism includes a latch spring engaging said rail member to lock said penetrating member in said extended position and a trigger responsive to distally-biased movement of said safety probe for releasing said latch spring.

6. A safety penetrating instrument as recited in claim 1 wherein said releasing means is responsive to distally-biased movement of said safety probe and said penetrating member upon penetrating into the anatomical cavity.

7. A safety penetrating instrument as recited in claim 6 and further comprising a rail member mounting a proximal end of said penetrating member, wherein said proximal end of said penetrating member includes a flange movable within said rail member and said locking and releasing mechanism includes a latch spring engaging said rail member to lock said penetrating member in said extended position and a trigger responsive to distally-biased movement of said penetrating member flange and said safety probe for releasing said latch spring.

8. A safety penetrating instrument as recited in claim 1 wherein said penetrating member distal end extends distally from a junction where a transverse dimension of said penetrating member changes and wherein said portal sleeve distal end is proximally spaced from said junction when said penetrating member is at rest in said locked penetrating member extended position.

9. A safety penetrating instrument as recited in claim 1 wherein said safety probe distal end is located distally of said penetrating member distal end when said safety probe is in said rest position and said penetrating member is at rest in said locked penetrating member extended position.

10. A safety penetrating instrument for establishing a portal in the wall of an anatomical cavity comprising a housing;

an elongate portal sleeve having a proximal end mounted by said housing and a distal end for introduction in the anatomical cavity, said portal sleeve being movable relative to said housing between an extended rest position and a proximally spaced retracted position;

portal sleeve bias means for biasing said portal sleeve distally toward said portal sleeve rest position;

a hollow penetrating member disposed within said portal sleeve and having a distal end for penetrating the anatomical cavity wall, said penetrating member being movable relative to said portal sleeve between an extended position where said distal end of said penetrating member protrudes distally from said distal end of said portal sleeve and a retracted position proximally spaced from said extended position;

a safety probe disposed within said penetrating member, said safety probe being movable relative to said penetrating member between an extended safety probe rest position protecting said penetrating member distal end when said penetrating member is retracted and a safety probe retracted position exposing said penetrating member distal end when said penetrating member is extended;

safety probe bias means for biasing said safety probe distally toward said safety probe rest position;

retracting means for moving said penetrating member from said penetrating member extended position to said penetrating member retracted position;

means for manually moving said penetrating member from said penetrating member retracted position to said penetrating member extended position;

locking means for locking said penetrating member in said penetrating member extended position and preventing proximal movement of said penetrating member during penetration of the anatomical cavity wall; and releasing means responsive to penetration of said safety penetrating instrument into the anatomical cavity for triggering release of said locking means to permit said retracting means to move said penetrating member proximally to said penetrating member retracted position.

11. A safety penetrating instrument as recited in claim 10 wherein said releasing means is responsive to distally-biased movement of said portal sleeve upon penetrating into the anatomical cavity.

12. A safety penetrating instrument as recited in claim 11 wherein said locking and releasing means includes a latch arm extending through said penetrating member and carrying a proximal latching protrusion for engaging said penetrating member to lock said penetrating member in said extended position and a distal triggering protrusion for being operatively engaged by an operating member carried by said portal sleeve to release said latching protrusion from said penetrating member.

13. A safety penetrating instrument as recited in claim 12 wherein said operating member includes a lever pivotally mounted on a finger extending proximally from said portal sleeve.

14. A safety penetrating instrument as recited in claim 10 wherein said releasing means is responsive to distally-biased movement of said safety probe upon penetrating into the anatomical cavity.

15. A safety penetrating instrument as recited in claim 14 and further comprising a rail member mounting a proximal end of said penetrating member, wherein said locking and releasing mechanism includes a latch spring engaging said rail member to lock said penetrating member in said extended position and a trigger responsive to distally-biased movement of said safety probe for releasing said latch spring.

16. A safety penetrating instrument as recited in claim 10 wherein said releasing means is responsive to distally-biased movement of said portal sleeve and said safety probe upon penetrating into the anatomical cavity.

17. A safety penetrating instrument as recited in claim 16 and further comprising a rail member mounting a proximal end of said penetrating member, wherein said locking and releasing mechanism includes a latch spring engaging said rail member to lock said penetrating member in said extended position and a trigger responsive to distally-biased movement of said safety probe for releasing said latch spring, and wherein said locking and releasing means further includes a latch arm extending through said penetrating member and carrying a proximal latching protrusion for engaging said rail member to lock said penetrating member in said extended position and a distal triggering protrusion for being operatively engaged by an operating member carried by said portal sleeve to release said latching protrusion from said penetrating member in response to distally-biased movement of said portal sleeve.

18. A safety penetrating instrument as recited in claim 10 wherein said penetrating member distal end extends distally from a junction where a transverse dimension of said penetrating member changes and wherein said portal sleeve distal end is aligned with said junction when said portal sleeve is in said rest position and said penetrating member is in said locked penetrating member extended position.

19. A safety penetrating instrument as recited in claim 10 wherein said penetrating member distal end extends distally from a junction where a transverse dimension of said penetrating member changes and wherein said portal sleeve distal end is located proximally of said junction when said portal sleeve is in said rest position and said penetrating member is in said locked penetrating member extended position.

20. A safety penetrating instrument as recited in claim 10 wherein said penetrating member distal end extends distally from a junction where a transverse dimension of said penetrating member changes and wherein said portal sleeve distal end is located distally of said junction when said portal sleeve is in said rest position and said penetrating member is in said locked penetrating member extended position.

21. A safety penetrating instrument as recited in claim 10 wherein said safety probe distal end is located distally of said penetrating member distal end when said safety probe is in said rest position and said penetrating member is in said locked penetrating member extended position.

22. A safety penetrating instrument for establishing a portal in the wall of an anatomical cavity comprising a housing;

an elongate portal sleeve having a proximal end mounted by said housing and a distal end for introduction in the anatomical cavity, said portal sleeve being movable relative to said housing between an extended rest position and a proximally spaced retracted position;

portal sleeve bias means for biasing said portal sleeve distally toward said portal sleeve rest position;

a hollow penetrating member disposed within said portal sleeve and having a distal end for penetrating the anatomical cavity wall, said penetrating member being movable relative to said portal sleeve between an extended position where said distal end of said penetrating member protrudes distally from said distal end of said portal sleeve and a retracted position proximally spaced from said extended position;

a safety probe disposed within said penetrating member, said safety probe being movable relative to said penetrating member between an extended safety probe rest position protecting said penetrating member distal end when said penetrating member is retracted and a safety probe retracted position exposing said penetrating member distal end when said penetrating member is extended;

safety probe bias means for biasing said safety probe distally toward said safety probe rest position;

retracting means for moving said penetrating member from said penetrating member extended position to said penetrating member retracted position;

means for manually moving said penetrating member from said penetrating member retracted position to said penetrating member extended position;

locking means for locking said penetrating member in said penetrating member extended position while permitting a predetermined amount of proximal movement of said penetrating member during penetration of the anatomical cavity wall;

penetrating member bias means for biasing said penetrating member distally in said locked penetrating member extended position to permit said penetrating member to move proximally during penetration of the anatomical cavity wall and distally upon introduction into the anatomical cavity; and releasing means responsive to penetration of said safety penetrating instrument into the anatomical cavity for triggering release of said locking means to permit said retracting means to move said penetrating member proximally to said penetrating member retracted position.

23. A safety penetrating instrument as recited in claim 22 wherein said releasing means is responsive to distally-biased movement of said penetrating member upon penetrating into the anatomical cavity.

24. A safety penetrating instrument as recited in claim 23 and further comprising a rail member mounting a proximal end of said penetrating member, wherein said locking and releasing mechanism includes a latch spring engaging said rail member to lock said penetrating member in said extended position and a trigger responsive to distally-biased movement of said penetrating member for releasing said latch spring.

25. A safety penetrating instrument as recited in claim 22 wherein said releasing means is responsive to distally-biased movement of said safety probe upon penetrating into the anatomical cavity.

26. A safety penetrating instrument as recited in claim 25 and further comprising a rail member mounting a proximal end of said penetrating member, wherein said locking and releasing mechanism includes a latch spring engaging said rail member to lock said penetrating member in said extended position and a trigger responsive to distally-biased movement of said safety probe for releasing said latch spring.

27. A safety penetrating instrument as recited in claim 22 wherein said releasing means is responsive to distally-biased movement of said portal sleeve upon penetrating into the anatomical cavity.

28. A safety penetrating instrument as recited in claim 27 wherein said locking and releasing means includes a latch arm extending through said penetrating member and carrying a proximal latching protrusion for engaging said penetrating member to lock said penetrating member in said extended position and a distal triggering protrusion for being engaged by an operating member carried by said portal sleeve to release said latching protrusion from said penetrating member.

29. A safety penetrating instrument as recited in claim 28 wherein said operating member includes a lever pivotally mounted on a finger extending proximally from said portal sleeve.

30. A safety penetrating instrument as recited in claim 22 wherein said releasing means is responsive to distally-biased movement of said portal sleeve and said penetrating member upon penetrating into the anatomical cavity.

31. A safety penetrating instrument as recited in claim 30 and further comprising a rail member mounting a proximal end of said penetrating member, wherein said locking and releasing mechanism includes a latch spring engaging said rail member to lock said penetrating member in said extended position and a trigger responsive to distally-biased movement of said penetrating member for releasing said latch spring, and wherein said locking and releasing means further includes a latch arm extending through said penetrating member and carrying a proximal latching protrusion for engaging said rail member to lock said penetrating member in said extended position and a distal triggering protrusion for being engaged by an operating member carried by said portal sleeve to release said latching protrusion from said penetrating member in response to distally-biased movement of said portal sleeve.

32. A safety penetrating instrument as recited in claim 22 wherein said releasing means is responsive to distally-biased movement of said portal sleeve and said safety probe upon penetrating into the anatomical cavity.

33. A safety penetrating instrument as recited in claim 32 and further comprising a rail member mounting a proximal end of said penetrating member, wherein said locking and releasing mechanism includes a latch spring engaging said rail member to lock said penetrating member in said extended position and a trigger responsive to distally-biased movement of said safety probe for releasing said latch spring, and wherein said locking and releasing means further includes a latch arm extending through said penetrating member and carrying a proximal latching protrusion for engaging said rail member to lock said penetrating member in said extended position and a distal triggering protrusion for being engaged by an operating member carried by said portal sleeve to release said latching protrusion from said penetrating member in response to distally-biased movement of said portal sleeve.

34. A safety penetrating instrument as recited in claim 22 wherein said releasing means is responsive to distally-biased movement of said safety probe and said penetrating member upon penetrating into the anatomical cavity.

35. A safety penetrating instrument as recited in claim 34 and further comprising a rail member mounting a proximal end of said penetrating member, wherein said locking and releasing mechanism includes a latch spring engaging said rail member to lock said penetrating member in said extended position and a trigger responsive to distally-biased movement of said penetrating member and said safety probe for releasing said latch spring.

36. A safety penetrating instrument as recited in claim 22 wherein said releasing means is responsive to distally-biased movement of said portal sleeve, said safety probe and said penetrating member upon penetrating into the anatomical cavity.

37. A safety penetrating instrument as recited in claim 36 and further comprising a rail member mounting a proximal end of said penetrating member, wherein said locking and releasing mechanism includes a latch spring engaging said rail member to lock said penetrating member in said extended position and a trigger responsive to distally-biased movement of said penetrating member and said safety probe for releasing said latch spring, and wherein said locking and releasing means further includes a latch arm extending through said penetrating member and carrying a proximal latching protrusion for engaging said rail member to lock said penetrating member in said extended position and a distal triggering protrusion for being engaged by an operating member carried by said portal sleeve to release said latching protrusion from said penetrating member in response to distally-biased movement of said portal sleeve.

38. A safety penetrating instrument as recited in claim 22 wherein said penetrating member distal end extends distally from a junction where a transverse dimension of said penetrating member changes and wherein said portal sleeve distal end is aligned with said junction when said portal sleeve is in said rest position and said penetrating member is in said locked penetrating member extended position.

39. A safety penetrating instrument as recited in claim 22 wherein said penetrating member distal end extends distally from a junction where a transverse dimension of said penetrating member changes and wherein said portal sleeve distal end is located proximally of said junction when said portal sleeve is in said rest position and said penetrating member is in said locked penetrating member extended position.

40. A safety penetrating instrument as recited in claim 22 wherein said penetrating member distal end extends distally from a junction where a transverse dimension of said penetrating member changes and wherein said portal sleeve distal end is located distally of said junction when said portal sleeve is in said rest position and said penetrating member is in said locked penetrating member extended position.

41. A safety penetrating instrument as recited in claim 22 wherein said safety probe distal end is located distally of said penetrating member distal end when said safety probe is in said rest position and said penetrating member is at rest in said locked penetrating member extended position.

42. A safety penetrating instrument for establishing a portal in the wall of an anatomical cavity comprising a housing;

an elongate portal sleeve having a proximal end mounted by said housing and a distal end for introduction into the anatomical cavity;

a hollow penetrating member disposed within said portal sleeve and having a distal end for penetrating the anatomical cavity wall, said penetrating member distal end having a partially conical configuration with partial threads;

a safety probe disposed within said penetrating member and having a distal end, said safety probe being movable relative to said penetrating member between an extended safety probe rest position protecting said penetrating member distal end and a safety probe retracted position exposing said penetrating member distal end, said safety probe distal end having a partially conical configuration with partial threads such that, when the safety probe is in the safety probe retracted position, the configuration of the safety probe distal end cooperates with the configuration of the penetrating member distal end to produce a substantially complete geometric cone configuration with external threads; and safety probe bias means for biasing said safety probe distally toward said safety probe rest position.

* * * * *